(12) United States Patent
Helle et al.

(10) Patent No.: US 11,155,568 B2
(45) Date of Patent: Oct. 26, 2021

(54) BIOADHESIVES

(71) Applicant: NUtech Ventures, Lincoln, NE (US)

(72) Inventors: Mark Alan Helle, Lincoln, NE (US);
Chin Li Cheung, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 27 days.

(21) Appl. No.: 16/698,166

(22) Filed: Nov. 27, 2019

(65) Prior Publication Data

US 2020/0095270 A1 Mar. 26, 2020

Related U.S. Application Data

(62) Division of application No. 15/552,227, filed as application No. PCT/US2016/018498 on Feb. 18, 2016, now Pat. No. 10,533,031.

(60) Provisional application No. 62/117,625, filed on Feb. 18, 2015.

(51) Int. Cl.
| | |
|---|---|
| *C07G 1/00* | (2011.01) |
| *C09J 163/00* | (2006.01) |
| *C09J 191/00* | (2006.01) |
| *C04B 24/18* | (2006.01) |
| *C09K 8/20* | (2006.01) |
| *C07C 245/20* | (2006.01) |
| *C07C 309/13* | (2006.01) |

(52) U.S. Cl.
CPC ............... *C07G 1/00* (2013.01); *C04B 24/18* (2013.01); *C09J 163/00* (2013.01); *C09J 191/00* (2013.01); *C09K 8/20* (2013.01); *C07C 245/20* (2013.01); *C07C 309/13* (2013.01)

(58) Field of Classification Search
CPC ...................................................... C09J 191/00
See application file for complete search history.

(56) References Cited

U.S. PATENT DOCUMENTS

| | | | |
|---|---|---|---|
| 2,657,205 A | 10/1953 | Johannes | |
| 3,836,518 A | 9/1974 | Clark | |
| 4,119,640 A * | 10/1978 | Hodakowski | C08G 59/1433 549/337 |
| 4,149,850 A | 4/1979 | Schlafer | |
| 4,846,888 A | 7/1989 | Detroit | |
| 5,055,532 A * | 10/1991 | Hoffman | C08F 299/026 525/528 |
| 9,102,801 B1 | 8/2015 | Detroit | |
| 2006/0117500 A1 | 6/2006 | Meler | |
| 2006/0177763 A1 * | 8/2006 | Matsuoka | C08F 8/00 430/270.1 |
| 2006/0281860 A1 * | 12/2006 | Higuchi | C08L 25/02 525/89 |

(Continued)

FOREIGN PATENT DOCUMENTS

| | | |
|---|---|---|
| RU | 2011668 | 4/1994 |
| WO | WO 2013/050661 | 4/2013 |

OTHER PUBLICATIONS

Meadows et al. (Medicinal Research Reviews, vol. 26, No. 6, 793-814, 2006) (Year: 2006).*

(Continued)

*Primary Examiner* — Liam J Heincer
(74) *Attorney, Agent, or Firm* — Fish & Richardson P.C.

(57) ABSTRACT

Materials and methods for preparing reactive lignin and for preparing a bio-based adhesive are described herein.

18 Claims, 8 Drawing Sheets

(56) References Cited

U.S. PATENT DOCUMENTS

| | | | | |
|---|---|---|---|---|
| 2008/0274133 | A1* | 11/2008 | Jakobsen | A61P 33/02 424/193.1 |
| 2010/0063215 | A1* | 3/2010 | Yano | C09J 171/02 525/326.5 |
| 2013/0164681 | A1 | 6/2013 | Hyung | |
| 2013/0289284 | A1* | 10/2013 | Musa | C07D 303/17 548/519 |
| 2014/0154506 | A1* | 6/2014 | Williams | C09J 7/38 428/355 R |
| 2014/0342153 | A1* | 11/2014 | Li | C09J 7/38 428/355 EP |
| 2016/0215088 | A1* | 7/2016 | Omonov | C08G 59/4238 |

OTHER PUBLICATIONS

'www.arb.ca' [online]. "Indoor Air Pollution in California," Jul. 2005, [retrieved on Sep. 6, 2017] https://www.arb.ca.gov/research/indoor/ab1173/rpt0705.pdf, pp. 65-70.

'www.iarc.fr' [online]. "Iarc Classifies Formaldehyde as Carcinogenic to Humans," Jun. 2004, [retrieved on Sep. 6, 2017]. Retrieved from the Internet: URL< http://www.iarc.fr/en/media-centre/pr/2004/pr153.html>, 2 pages.

'www.marketresearch.com' [online]. "Reconstituted Wood Product Manufacturing Industry in the U.S. and its International Trade," Oct. 2016, [retrieved on Sep. 7, 2017]. Retrieved from the Internet: URL <https://www.marketresearch.com/Supplier-Relations-US-LLC-v3418/Reconstituted-Wood-Product-Manufacturing-International-10351472/>. 6 pages.

Ahmad et al., "Synthesis and Applications of Three Vinylsulfone Based Fiber-reactive azo Dyes for Dyeing Cotton Fabric," International Journal of Basic & Applied Sciences, 2012, 12(6): 129-136.

Christie, Colour Chemistry, Second Edition, 2001, 372 pages.

Dave et al., "Synthesis and characterization novel oligomeric azo dye," Journal of Chemical and Pharmaceutical Research, 2013, 5(3): 112-116.

Duval and Lawoko, "A review on lignin-based polymeric, micro- and nano-structured materials," React. Func. Polymers, Dec. 2014, 85:78-96.

El Mansouri & Salvado, "Structural characterization of technical lignins for the production of adhesives: Application to lignosulfonate, kraft, soda-anthraquinone, organosolv and ethanol process lignins," Industr. Crops Prod., Jul. 2006, 24:8-16.

Ge et al., "Dithiocarnamate functionalized lignin for efficient removal of metallic ions and the usage of the metal-loaded bio-sorbents as potential free radical scavengers," J. Mat. Chem. A, 2014, 2:2136-45.

Ge et al., Heavy metal ions retention by bi-functionalized lignin: Synthesis, applications, and adsorption mechanisms, J. Industr. Eng. Chem., 2014, 20:4429-36.

International Preliminary Report on Patentability in International Application No. PCT/US2016/018498, dated Aug. 22, 2017, 11 pages.

International Search Report and Written Opinion in International Application No. PCT/US2016/018498, dated Jun. 24, 2016, 14 pages.

Laurichesse and Averous, Chemical modification of lignins: Towards bio-based polymers, Progress in Polymer Science, 2014, 39:1266-90.

Li et al., "Surface-Functionalized Porous Lignin for Fast and Efficient Lead Removal from Aqueous Solution," ACS App. Mat. Interfac., 2015, 7:15000-9.

Liu et al., "Green" Composites from Renewable Resources: Preparation of Epoxidized Soybean Oil and Flax Fiber Composites, J. Agric. Food Chem., 2006, 54(6):2134-7.

Mulder et al., "Lignin based controlled release coatings," Industr. Crops Prod., Jul. 2011, 34:915-20.

Nair et al., "Addition curable phenolic resins based on ethynyl phenyl azo functional novolac," Polymer, 2002, 43: 2609-2617.

Norgren and Edlund, "Lignin: Recent advances and emerging applications," Curr. Opin. Coll. Interf. Sci., 2014, 19:409-16.

Ravalli et al., "Sustainable Epoxy Materials From Vegetable Oils," 2013 Rensselaer Nanotechnology Center Research Symposium, 2013, 16 pages.

Saithai et al., "Effects of different epoxidation methods of soybean oil on the characteristics of acrylated epoxidized soybean oil-co-poly(methyl methacrylate) copolymer," eXPRESS Polymer Lett., 2013, 7: 910-924.

Saremi et al., "Epoxidation of Soybean Oil," Annals of Biol. Res., 2012, 3: 4254-4258.

Thakur & Thakur, "Recent advances in green hydrogels from lignin: a review," Intern. J. Biol. Macromol., 2015, 72:834-47.

Wang and Zhao, Encapsulation of the Herbicide Picloram by Using Polyelectrolyte Biopolymers as Layer-by-Layer Materials, J. Agric. Food Chem., 2013, 61:3789-96.

Xing et al., "Functionalized lignin for halogen-free flame retardant rigid polyurethane foam: preparation, thermal stability, fire performance and mechanical properties," J. Poly. Res., 2013, 20:234.

\* cited by examiner

Epoxidized vegetable oil        Vinyl sulfone precursor

Vegetable oil based cross-linking agent

Vegetable oil based cross-linked cellulose

BIOADHESIVES

CLAIM OF PRIORITY

This application claims priority to U.S. patent application Ser. No. 15/552,227, filed on Aug. 18, 2017, which is a U.S. National Application of PCT/US2016/018498 filed on Feb. 18, 2016, which claims priority to U.S. Provisional Application 62/117,625 filed on Feb. 18, 2015, the entire contents of which are hereby incorporated by reference.

TECHNICAL FIELD

This disclosure generally relates to methods of making and using reactive lignin. This disclosure also generally relates to methods of making and using bio-based adhesives.

BACKGROUND

Lignin is the second most abundant natural polymer behind cellulose, yet lignin has very little commercial value despite years of research. Lignin is one of the major components of the cell wall in wood and other plant based materials such as hemp or crop wastes. It is produced in enormous quantities each year, primarily as a by-product in the pulp and paper industries. Lignin has little economic value and the majority of lignin is burned as a low grade fuel or is discharged into the aquatic ecosystem as waste, causing a significant impact on the environment. For example, the majority of the Biological Oxygen Demand (BOD) from pulp mill effluents is due to waste lignin. In addition, an increase in the production of cellulosic ethanol from corn stalk and other biomass resources will add significantly to this glut of lignin.

This tremendous oversupply of lignin presents an enormous opportunity for the development of renewable biomaterials to replace non-biodegradable petroleum-based products, and the present disclosure provides for commercially-viable and inexpensive methods of making reactive lignin that can be used to make a wide variety of lignin-based products.

In a similar vein, there is a growing demand for developing non-petroleum-based materials to replace traditional plastics. There is a critical need to replace the commonly used formaldehyde-based resins found in many building materials such as plywood and particle boards. Formaldehyde-based resins have raised alarming health concerns because formaldehyde is highly toxic, allergenic and a classified carcinogenic. The off-gassing of formaldehyde-based resins is a significant source of indoor air pollution, particularly from formaldehyde pressed-wood products.

Thus, this disclosure also describes the development of a class of formaldehyde-free, bio-based reactive adhesives for binding renewable biodegradable material such as lignin, cellulose, wood chips and crop waste to fabricate useful solid materials and composites.

SUMMARY

Materials and methods for preparing reactive lignin are described herein. In addition, bio-based adhesives and methods of making such bio-based adhesives are described herein.

In one aspect, a process for preparing a lignin derivative is provided. Such a process typically includes contacting a lignin with a diazonium compound of Formula I:

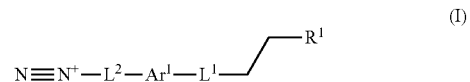

(I)

wherein $Ar^1$ is a 6-10 membered aryl substituted by 1, 2, 3, or 4 independently selected $R^a$ groups; $L^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-; $R^1$ is selected from the group consisting of —O—S(O)$_2$OH and —O—S(O)$_2$OR$^a$; $L^2$ is selected from the group consisting of a bond, —C1-6 alkylene-, 6-10 membered aryl, 5-10 membered heteroaryl, wherein the 6-10 membered aryl, 5-10 membered heteroaryl is optionally substituted by 1, 2, 3, or 4 independently selected $R^b$ groups; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each $R^a$ is independently selected from the group consisting of $C_{1-6}$ alkyl, 6-10 membered aryl, 5-10 membered heteroaryl, wherein the 6-10 membered aryl, 5-10 membered heteroaryl is optionally substituted by 1, 2, 3, or 4 independently selected $R^b$ groups; each $R^b$ is independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy; each $R^c$ is independently selected from the group consisting of H and $C_{1-3}$ alkyl.

In some embodiments, the diazonium compound of Formula I is a compound of formula Ia:

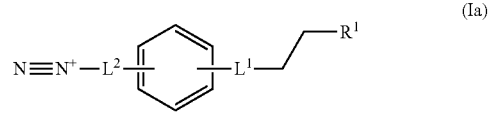

(Ia)

wherein: $L^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-; $R^1$ is selected from the group consisting of —O—S(O)$_2$OH and —O—S(O)$_2$OR$^a$; $L^2$ is selected from the group consisting of a bond, —$C_{1-6}$ alkylene-, 6-10 membered aryl, 5-10 membered heteroaryl, wherein the 6-10 membered aryl, 5-10 membered heteroaryl is optionally substituted by 1, 2, 3, or 4 independently selected $R^b$ groups; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each $R^a$ is independently selected from the group consisting of $C_{1-6}$ alkyl, 6-10 membered aryl, 5-10 membered heteroaryl, wherein the 6-10 membered aryl, 5-10 membered heteroaryl is optionally substituted by 1, 2, 3, or 4 independently selected $R^b$ groups; each $R^b$ is independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy; and each $R^c$ is independently selected from the group consisting of H and $C_{1-3}$ alkyl.

In some embodiments, the diazonium compound of Formula I is a compound of formula Ib:

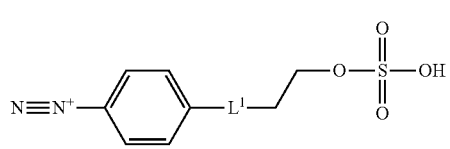

(Ib)

wherein: $L^1$ is selected from the group consisting of —$C_{1-6}$ alkylene-, —Y—$C_{1-6}$ alkylene-, —Y—$C_{1-6}$ alkylene-Y—, and —$C_{1-4}$ alkylene-Y—$C_{1-4}$ alkylene-; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each R is independently selected from the group consisting of H and $C_{1-3}$ alkyl.

In some embodiments, the diazonium compound of Formula I is a compound of formula Ic:

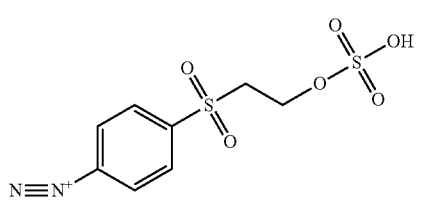

(Ic)

In some embodiments, the contacting is performed in an aqueous solution. In some embodiments, the aqueous solution has a pH of less than about 7. In some embodiments, the aqueous solution has a pH of about 4 to about 5.

In some embodiments, such a process further includes forming the diazonium compound from the corresponding amine precursor prior to contacting the lignin with the diazonium compound. In some embodiments, forming the diazonium compound from the corresponding amine precursor comprises contacting the amine precursor with nitrous acid.

In some embodiments, such a method further includes contacting the lignin derivative with a basic aqueous solution to form an alkene lignin derivative of Formula II:

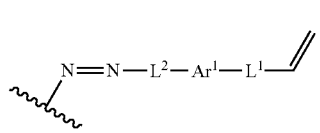

II wherein: Ar$^1$ is a 6-10 membered aryl substituted by 1, 2, 3, or 4 independently selected R$^a$ groups; L$^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-; L$^2$ is selected from the group consisting of a bond, —$C_{1-6}$ alkylene-, 6-10 membered aryl, 5-10 membered heteroaryl, wherein the 6-10 membered aryl, 5-10 membered heteroaryl is optionally substituted by 1, 2, 3, or 4 independently selected R$^b$ groups; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each R$^a$ is independently selected from the group consisting of $C_{1-6}$ alkyl, 6-10 membered aryl, 5-10 membered heteroaryl, wherein the 6-10 membered aryl, 5-10 membered heteroaryl is optionally substituted by 1, 2, 3, or 4 independently selected R$^b$ groups; each R$^b$ is independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy; and each R$^c$ is independently selected from the group consisting of H and $C_{1-3}$ alkyl; and the wavy line indicates the point of attachment to a phenyl group of the lignin.

In some embodiments, the alkene lignin derivative of Formula II is a compound of formula IIa:

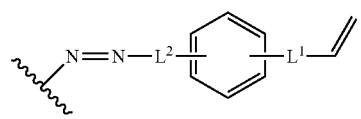

(IIa)

wherein: L$^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-; L$^2$ is selected from the group consisting of a bond, —$C_{1-6}$ alkylene-, 6-10 membered aryl, 5-10 membered heteroaryl, wherein the 6-10 membered aryl, 5-10 membered heteroaryl is optionally substituted by 1, 2, 3, or 4 independently selected R$^b$ groups; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each R$^b$ is independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy; and each R$^c$ is independently selected from the group consisting of H and $C_{1-3}$ alkyl; and the wavy line indicates the point of attachment to a phenyl group of the lignin.

In some embodiments, the alkene lignin derivative of Formula II is a compound of formula IIb:

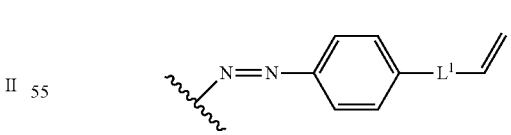

(IIb)

wherein: L$^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each R$^c$ is independently selected from the group consisting of H and $C_{1-3}$ alkyl; and the wavy line indicates the point of attachment to a phenyl group of the lignin.

In some embodiments, the alkene lignin derivative of Formula II is a compound of formula IIc:

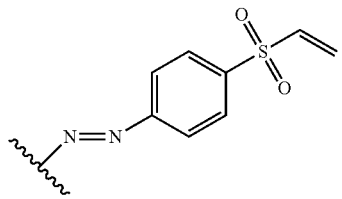
(IIc)

wherein the wavy line indicates the point of attachment to a phenyl group of the lignin.

In some embodiments, the basic aqueous solution has a pH of about 8 to about 12. In some embodiments, contacting the lignin derivative with the basic aqueous solution to form the alkene lignin derivative is performed at a temperature of at least about 50° C. In some embodiments, contacting the lignin derivative with the basic aqueous solution to form the alkene lignin derivative is performed at a temperature of about 60° C. to about 80° C.

In some embodiments, such a method further includes contacting the alkene lignin derivative with a nucleophilic compound to form a functionalized lignin. Representative nucleophilic compounds include, without limitation, a polyalcohol, a sugar alcohol, a monosaccharide, a disaccharide, an oligosaccharide, a polysaccharide, a polyether, and mixtures thereof. In some embodiments, the nucleophilic compound comprises at least one functional group selected from group consisting of —OH, —NH$_2$, —SH, —ONH$_2$, and —NHOH.

In some embodiments, the functionalized lignin is a compound of formula III:

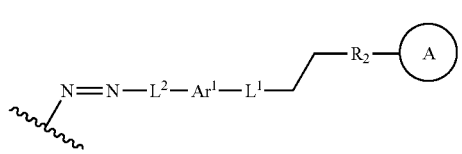
III wherein Ar$^1$ is a 6-10 membered aryl substituted by 1, 2, 3, or 4 independently selected R$^a$ groups; L$^1$ is selected from the group consisting of —C$_{1-6}$ alkylene-, —Y—, —Y—C$_{1-6}$ alkylene-, —Y—C$_{1-6}$ alkylene-Y—, and —C$_{1-4}$ alkylene-Y—C$_{1-4}$ alkylene-; L$^2$ is selected from the group consisting of a bond, —C$_{1-6}$ alkylene-, 6-10 membered aryl, 5-10 membered heteroaryl, wherein the 6-10 membered aryl, 5-10 membered heteroaryl is optionally substituted by 1, 2, 3, or 4 independently selected R$^b$ groups; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each R$^a$ is independently selected from the group consisting of C$_{1-6}$ alkyl, 6-10 membered aryl, 5-10 membered heteroaryl, wherein the 6-10 membered aryl, 5-10 membered heteroaryl is optionally substituted by 1, 2, 3, or 4 independently selected R$^b$ groups; each R$^b$ is independently selected from the group consisting of OH, NO$_2$, CN, SH, halo, C$_{1-6}$ alkyl, C$_{2-6}$ alkenyl, C$_{2-6}$ alkynyl, C$_{1-4}$ haloalkyl, and C$_{1-6}$ alkoxy; and each R$^c$ is independently selected from the group consisting of H and C$_{1-3}$ alkyl; the wavy line indicates the point of attachment to a phenyl group of the lignin; Z is selected from the group consisting of —O—, —NH—, —S—, —ONH—, and —NHO—; and group A is the nucleophilic compound.

In another aspect, a process for preparing a functionalized lignin is provided. Such a process typically includes (i) contacting a lignin with a diazonium compound of Formula I to form a lignin derivative,

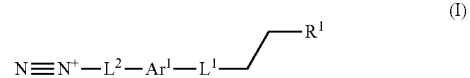
(I)

wherein: Ar$^1$ is a 6-10 membered aryl substituted by 1, 2, 3, or 4 independently selected R$^a$ groups; L$^1$ is selected from the group consisting of —C$_{1-6}$ alkylene-, —Y—, —Y—C$_{1-6}$ alkylene-, —Y—C$_{1-6}$ alkylene-Y—, and —C$_{1-4}$ alkylene-Y—C$_{1-4}$ alkylene-; R$^1$ is selected from the group consisting of —O—S(O)$_2$OH and —O—S(O)$_2$OR$^a$; L$^2$ is selected from the group consisting of a bond, —C 1-6 alkylene-, 6-10 membered aryl, 5-10 membered heteroaryl, wherein the 6-10 membered aryl, 5-10 membered heteroaryl is optionally substituted by 1, 2, 3, or 4 independently selected R$^b$ groups; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each R$^a$ is independently selected from the group consisting of C$_{1-6}$ alkyl, 6-10 membered aryl, 5-10 membered heteroaryl, wherein the 6-10 membered aryl, 5-10 membered heteroaryl is optionally substituted by 1, 2, 3, or 4 independently selected R$^b$ groups; each R$^b$ is independently selected from the group consisting of OH, NO$_2$, CN, SH, halo, C$_{1-6}$ alkyl, C$_{2-6}$ alkenyl, C$_{2-6}$ alkynyl, C$_{1-4}$ haloalkyl, and C$_{1-6}$ alkoxy; each R$^c$ is independently selected from the group consisting of H and C$_{1-3}$ alkyl; (ii) contacting the lignin derivative with a basic aqueous solution to form an alkene lignin derivative of Formula II:

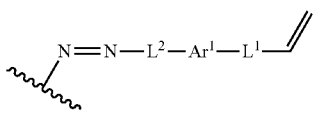

wherein the wavy line indicates a point of attachment to a phenyl group of the lignin; and (iii) contacting the alkene lignin derivative with a nucleophilic compound to form a functionalized lignin.

In still another aspect, a process for preparing a functionalized lignin is provided. Such a process typically includes: (i) contacting a lignin with a diazonium compound of Formula Ic to form a lignin derivative,

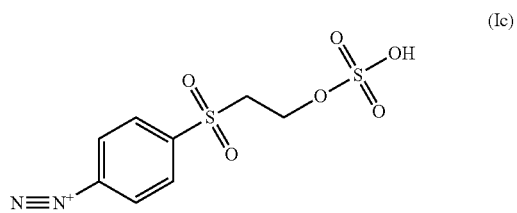 [SMILES: N#[N+]c1ccc(S(=O)(=O)CCOS(=O)(=O)O)cc1]
(Ic)

wherein the contacting is performed in an aqueous solution having a pH of about 4 to about 5; (ii) contacting the lignin derivative with a basic aqueous solution at a temperature of about 60° C. to about 80° C. to form an alkene lignin derivative of Formula IIc

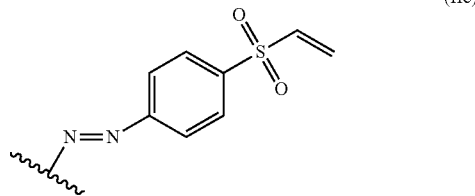
(IIc)

wherein: the wavy line indicates the point of attachment to a phenyl group of the lignin; the basic aqueous solution has a pH of about 8 to about 12; and (iii) contacting the alkene lignin derivative with a nucleophilic compound to form a functionalized lignin.

In yet another aspect, a compound of Formula IV is provided

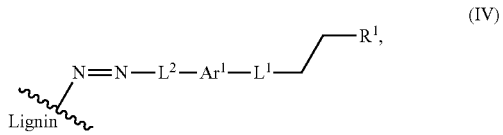
(IV)

wherein: $Ar^1$ is a 6-10 membered aryl substituted by 1, 2, 3, or 4 independently selected $R^a$ groups; $L^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-; $R^1$ is selected from the group consisting of —O—S(O)$_2$OH and —O—S(O)$_2$OR$^a$; $L^2$ is selected from the group consisting of a bond, —C 1-6 alkylene-, 6-10 membered aryl, 5-10 membered heteroaryl, wherein the 6-10 membered aryl, 5-10 membered heteroaryl is optionally substituted by 1, 2, 3, or 4 independently selected $R^b$ groups; each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$; each $R^a$ is independently selected from the group consisting of $C_{1-6}$ alkyl, 6-10 membered aryl, 5-10 membered heteroaryl, wherein the 6-10 membered aryl, 5-10 membered heteroaryl is optionally substituted by 24 1, 2, 3, or 4 independently selected $R^b$ groups; each $R^b$ is independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy; each $R^c$ is independently selected from the group consisting of H and $C_{1-3}$ alkyl; and the wavy line indicates the point of attachment to a phenyl group of a lignin.

In another aspect, a compound of Formula V is provided:

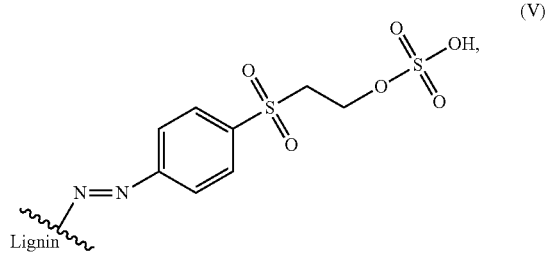 [SMILES: */N=N/c1ccc(S(=O)(=O)CCOS(=O)(=O)O)cc1]
(V)

wherein the wavy line indicates the point of attachment to a phenyl group of a lignin.

In one aspect, a bioadhesive is provided. Such a bioadhesive typically includes an epoxidized vegetable oil and a vinyl sulfone precursor. Representative vegetable oils include, without limitation, soybean oil, peanut oil, canola oil, crambe oil, lesquerella oil, meadowfoam oil, rapeseed oil, sunflower oil, tall oil, sesame oil, corn oil, linseed oil, and combinations thereof.

In another aspect, a method of making a bioadhesive is provided. Such a method typically includes combining an epoxidized vegetable oil with a vinyl sulfone precursor, to thereby make a bioadhesive. In some embodiments, the combining is performed under basic conditions. Representative basic conditions include a pH of between about 8 and about 10. In some embodiments, the combining is performed under mild heat. Representative mild heat includes a temperature of about 35° C. to about 85° C. Generally, the combining is performed in the absence of an organic solvent.

In yet another aspect, a method of making a biocomposite material is provided. Such a method typically includes combining a bioadhesive as described herein with a natural material to form a biocomposite material. Such a method further can include applying pressure. Typically, the combining is performed in the absence of an organic solvent. Typically, the bio-composite material is formaldehyde free.

Natural materials include, without limitation, wood shavings, wood chips, wood particles, pinewood shavings, hemp, waste cotton, other crop wastes. Bio-composite materials include, without limitation, wood composite boards, particle board, plywood, and packaging materials. Bio-composite materials also include, without limitation, absorbents, superabsorbents, bio-gels, and drug-release vehicles.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A: Reactive Lignin

Part B: Bio-Based Adhesives

Figure 8A:
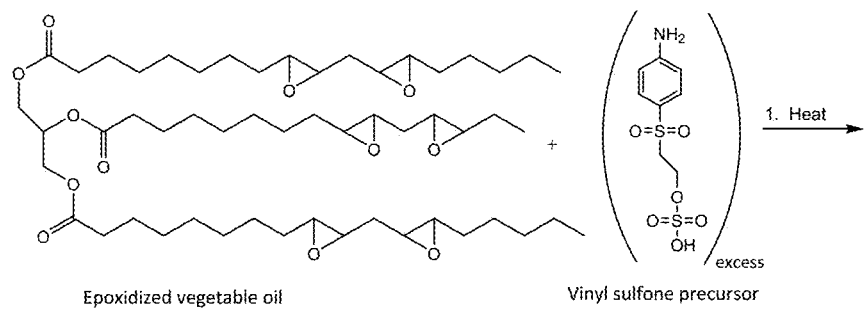
Figure 8B:
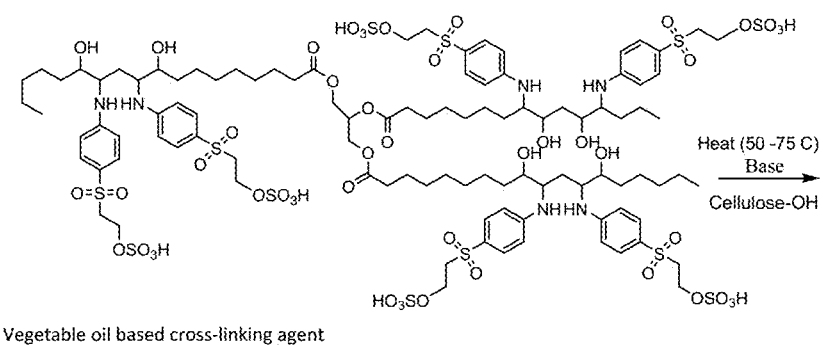
Figure 8C:
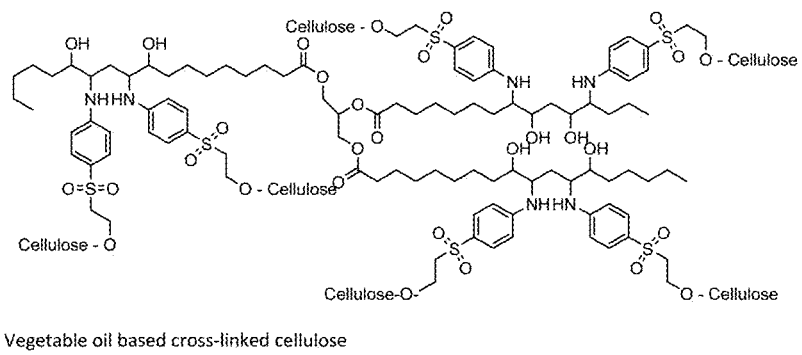

FIG. 8A-8C is a synthetic scheme for making a bio-based adhesive as described herein and for making bio-composite materials as described herein.

Figure 9:
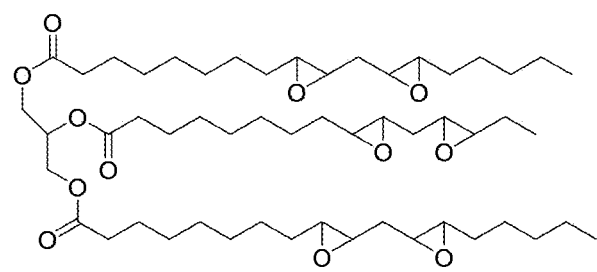

FIG. 9 is the chemical structure of an exemplary epoxidized vegetable oil.

Figure 10:
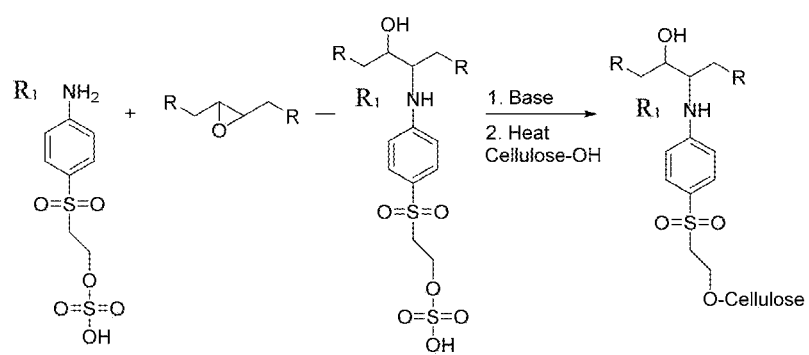

FIG. 10 is an exemplary reaction scheme for the methods described herein.

Figure 11:
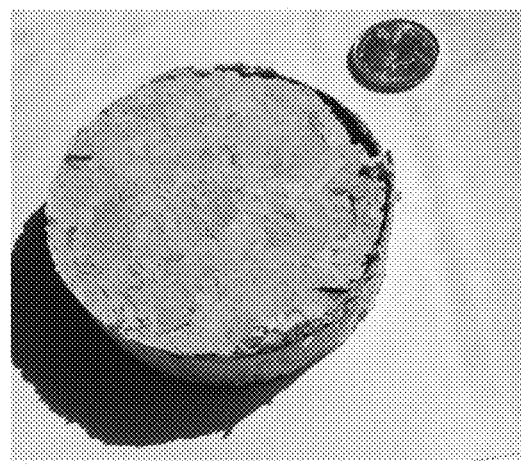

FIG. 11 is a photograph of a bio-composite disk made of wood shavings using the methods and materials disclosed herein (compared to a US quarter).

DETAILED DESCRIPTION

Part A: Reactive Lignin

Figure 1:
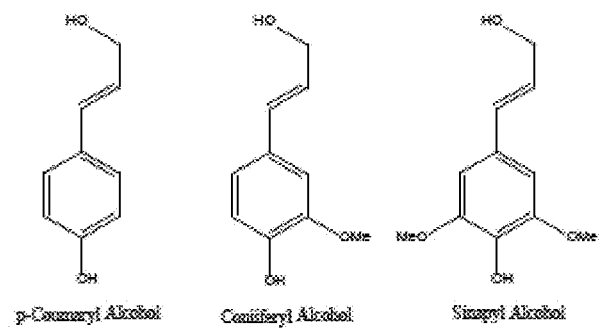
FIG. 1 is a schematic of the structures of p-coumaryl alcohol, coniferyl alcohol and sinapyl alcohol.
Figure 2:
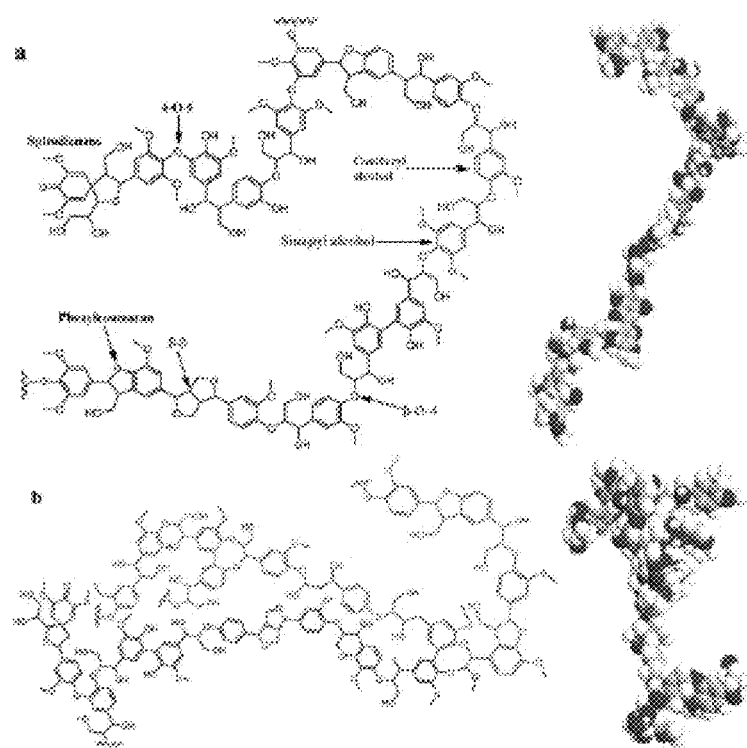
FIG. 2 shows the 2D chemical structures (left) and the 3D ball-and-stick models (right) of lignin from (a) hardwood and (b) softwood.

Lignin has enormous potential as a feedstock for the production of renewable biomaterials. Lignin is comprised of polymerized phenylpropane units linked through a number of different motifs of covalent bonds. Three of the common monomers of lignin are p-coumaryl alcohol, coniferyl alcohol and sinapyl alcohol, which are shown in FIG. 1. These monomeric alcohols, along with other minor lignin alcohols, are present in varying amounts in the polymer matrix, depending on the source of the lignin. The monolignol units are linked together via coupling reactions to form a complex three-dimensional molecular architecture. Typical segments of a lignin molecule are depicted in FIG. 2.

The main obstacle in developing commercially viable materials from lignin has been how to best make the appropriate chemical modifications for the desired purpose or structural properties. While many aromatic substitution reactions require harsh conditions and/or water sensitive catalysts, reactions with aryl diazonium salts take place in water under neutral or slightly basic pH ranges and at ambient temperatures.

The prior art describes a number of derivatives of lignin that have been prepared for various uses. For example, a Mannich reaction with formaldehyde was used to prepare a dithiocarbamate terminated lignin derivative for scavenging heavy metal ions (Ge et al., 2014, J. Mat. Chem. A, 2:2136-45), and a similar approach was used to attach both amine and sulfonic acid groups on lignin for heavy metal scavenging (Ge et al., 2014, J. Industr. Eng. Chem., 20:4429-36; Li et al., 2015, ACS App. Mat. Interfac., 7:15000-9). Phosphate groups also have been incorporated into lignin to prepare halogen free flame retardants (Xing et al., 2013, J. Poly. Res., 20:234), and lignin has undergone esterification with fatty acid chains to prepare waxy coatings for paper products (WO 2013/050661). Further, lignin has been used to make bio-based adhesives using formaldehyde-based resins (El Mansouri & Salvado, 2006, Industr. Crops Prod., 24:8-16), and efforts to prepare lignin-derived hydrogels have been reviewed (Thakur & Thakur, 2015, Intern. J. Biol. Macromol., 72:834-47). Additionally, lignin has been used for the controlled release of fertilizer (Mulder et al., 2011, Industr. Crops Prod., 34:915-20) and herbicides (Wang & Zhao, 2013, J. Agric. Food Chem., 61:3789-96) into the soil.

Several reviews describing current efforts to prepare value-added products from lignin have been published (Laurichesse & Averous, 2014, 39:1266-90; Duval & Lawoko, 2014, React. Func. Polymers, 85:78-96; Norgren & Edlund, 2014, Curr. Opin. Coll. Interf. Sci., 19:409-16), and the intensification of research efforts into value-added products from lignin was made evident by a review issue in the journal Green Chemistry devoted entirely to lignin-based chemistry (Lignin Chemistry and Valorization, Green Chem., 10:1). The methods described herein allow for lignin to be chemically modified easily and inexpensively such that it can be used in numerous applications; the methods described herein are expected to play a major role in the utilization of lignin for economical and practical applications.

Figure 3:
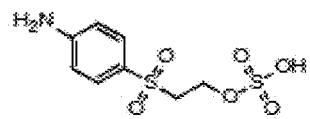
FIG. 3 is the structure of an aromatic amine with a sulfato-ethyl sulfone group.

The present document demonstrates that the aromatic rings within lignin provide sites for electrophilic aromatic substitution reactions. This disclosure describes the use of a diazonium salt prepared from a bifunctional aromatic amine to make reactive lignin. This chemistry is water-based and it requires no organic solvents. This class of molecules is used extensively in the dye industry. In addition to the amine, the other site capable of reactivity is the nascent vinyl sulfone group, which becomes activated under basic conditions (pH 8-12) and elevated temperatures (60-80° C.). One example of this class of molecules is depicted in FIG. 3.

Figure 4:
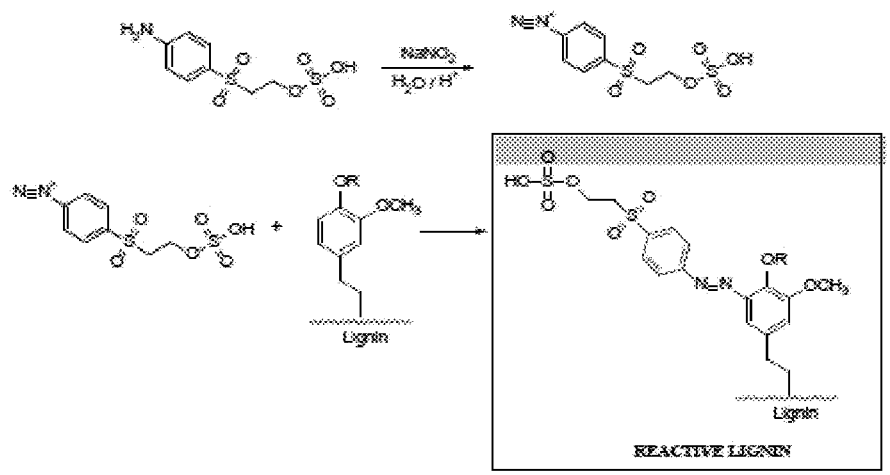
FIG. 4 shows the reaction scheme for the preparation of reactive lignin (R═H, OMe).

Preparation of a reactive lignin as described herein is illustrated in FIG. 4. As shown in FIG. 4, the aromatic amine reacts with nitrous acid, which is formed by treatment of sodium nitrite with acid. The reaction produces the diazonium salt, which then reacts with the aromatic rings in lignin to produce the azo compound. Since a color change is typically observed when a diazonium salt reacts with an aromatic ring to form the azo product, the deep purple color change in these reactions provides an indication of the success of the coupling reaction.

Figure 5:
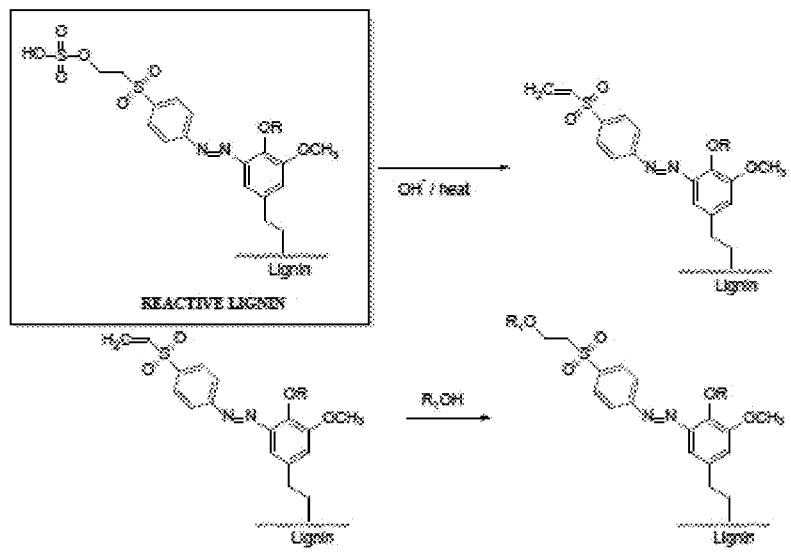
FIG. 5 shows a representative reaction scheme for the reaction of nucleophiles with reactive lignin.

Importantly, the sulfato-ethyl sulfone group is stable when exposed to the conditions under which the above-reaction takes place, but is activated when treated with a base at elevated temperatures. When activated, the sulfate ion is eliminated and a vinyl sulfone group is formed. The vinyl sulfone group acts as a Michael acceptor, and nucleophilic groups such as hydroxyls or amines will readily form a new covalent bond with the terminal carbon as depicted in FIG. 5. If the R group possesses more than one nucleophile, cross-linking can take place.

Figure 6:
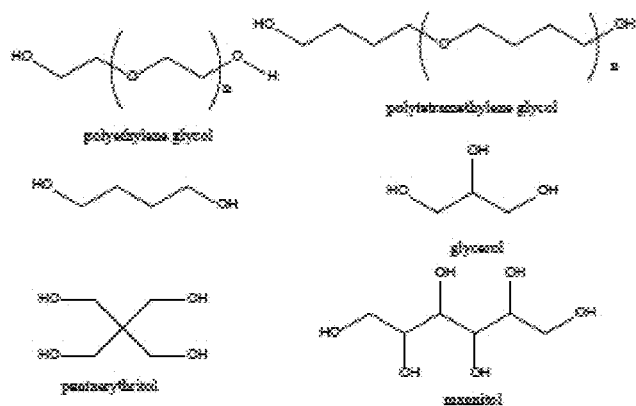
FIG. 6 shows the structures of potential polyols for lignin functionalization.
Figure 7:
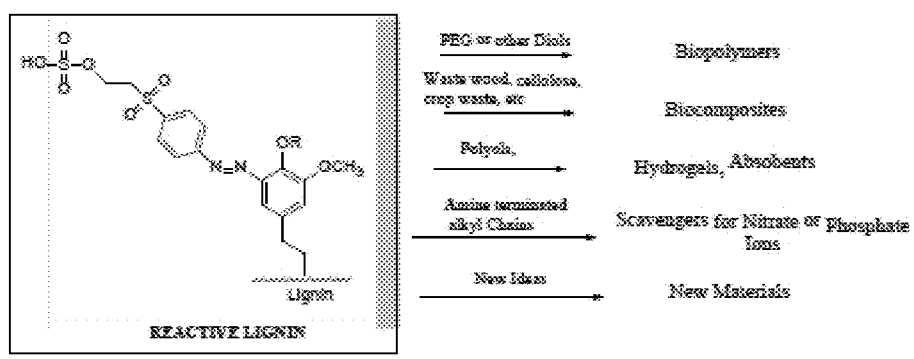
FIG. 7 shows exemplary potential applications for reactive lignin.

The methods described herein can be applied in numerous ways to prepare value added products from lignin. Representative examples are shown in FIG. 7. A few examples of areas in which the described methods can be applied include, without limitation, reaction with polyethylene glycol or polytetramethylene glycol for the fabrication of lignin co-polymers or the reaction with long chain fatty alcohols for hydrophobic coatings. Reactions with glycerol, mannitol, pentaerythritol or other inexpensive polyols (FIG. 6) can be used for cross-linking or to provide multiple reactive sites for further functionalization, thereby leading to hydrogels and absorbents. The same polyols can be used in concert with inexpensive bio-polymers such as, without limitation, cellulose, chitosan, starch or gelatin to prepare new renewable, biodegradable biomaterials. There are a number of polyamines that can be used in a similar manner. In addition, the reactive lignin described herein can be used to produce absorbents or superabsorbents for use, simply by way of example, in the medical industry (e.g., drug delivery, wound healing). The physical properties of the materials derived from these reactions can be manipulated by the number of equivalents of diazonium salts used, the molecular weights of the polymers, and/or the number of equivalents of the polyols used.

The present application provides, inter alia, a process for preparing a lignin derivative. The process includes contacting a lignin with a diazonium compound of Formula I:

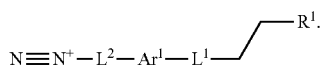

(I)

or a salt thereof. $Ar^1$ is a 6-10 membered aryl substituted by 1, 2, 3, or 4 independently selected $R^a$ groups. $L^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-. $R^1$ is selected from the group consisting of —O—S(O)$_2$OH and —O—S(O)$_2$OR$^a$. $L^2$ is selected from the group consisting of a bond, —$C_{1-6}$ alkylene-, 6-10 membered aryl, 5-10 membered heteroaryl, wherein the 6-10 membered aryl, 5-10 membered heteroaryl is optionally substituted by 1, 2, 3, or 4 independently selected $R^b$ groups. Each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each $R^a$ is independently selected from the group consisting of $C_{1-6}$ alkyl, 6-10 membered aryl, 5-10 membered heteroaryl, wherein the 6-10 membered aryl, 5-10 membered heteroaryl is optionally substituted by 1, 2, 3, or 4 independently selected $R^b$ groups. Each $R^b$ is independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy. Each $R^c$ is independently selected from the group consisting of H and $C_{1-3}$ alkyl.

In some embodiments, $L^1$ is —Y— and —Y— is S(O)$_2$. In some embodiment, $L^2$ is a bond.

Contacting a lignin with a compound of Formula I can result in the azo coupling of the compound of Formula I to a phenyl of the lignin as shown, for example, in FIG. 4 and Formula I-1:

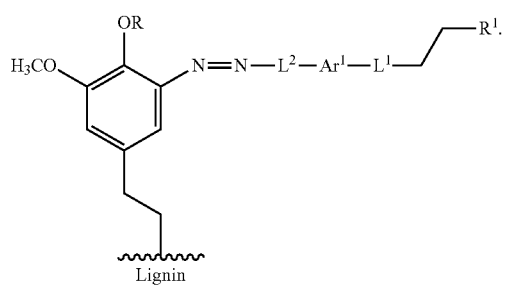

(I-1)

In some embodiments, the diazonium compound of Formula I can be a compound of formula Ia:

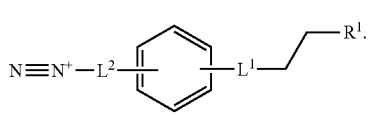

(Ia)

or a salt thereof. $L^1$ can be selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-. $R^1$ can be selected from the group consisting of —O—S(O)$_2$OH and —O—S(O)$_2$OR$^a$. $L^2$ can be selected from the group consisting of a bond, —$C_{1-6}$ alkylene-, 6-10 membered aryl, 5-10 membered heteroaryl, wherein the 6-10 membered aryl, 5-10 membered heteroaryl can be optionally substituted by 1, 2, 3, or 4 independently selected $R^b$ groups. Each Y can be independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each $R^a$ can be independently selected from the group consisting of $C_{1-6}$ alkyl, 6-10 membered aryl, 5-10 membered heteroaryl, wherein the 6-10 membered aryl, 5-10 membered heteroaryl can be optionally substituted by 1, 2, 3, or 4 independently selected $R^b$ groups. Each $R^b$ can be independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy. Each $R^c$ can be independently selected from the group consisting of H and $C_{1-3}$ alkyl.

In some embodiments, $L^1$ is —Y— and —Y— is S(O)$_2$. In some embodiment, $L^2$ is a bond.

In some embodiments, the diazonium compound of Formula I is a compound of formula Ib:

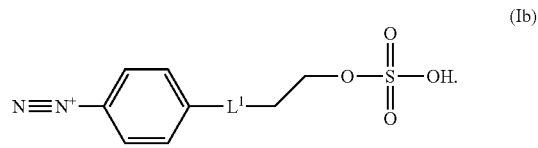

(Ib)

or a salt thereof. $L^1$ can be selected from the group consisting of —$C_{1-6}$ alkylene-, —Y—$C_{1-6}$ alkylene-, —Y—$C_{1-6}$ alkylene-Y—, and —$C_{1-4}$ alkylene-Y—$C_{1-4}$ alkylene-. Each Y can be independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. $R^c$ can be independently selected from the group consisting of H and $C_{1-3}$ alkyl.

In some embodiments the diazonium compound of Formula I is a compound of formula Ic:

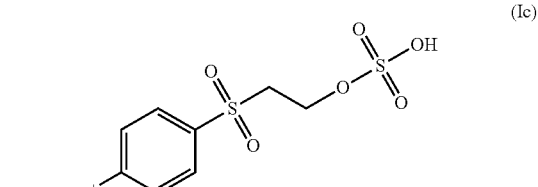

(Ic)

or a salt thereof.

Contacting a lignin with a compound of Formula Ic can result in the azo coupling of the compound of Formula Ic to an aromatic moiety of the lignin as shown, for example, in FIG. 4 and Formula Ic-1:

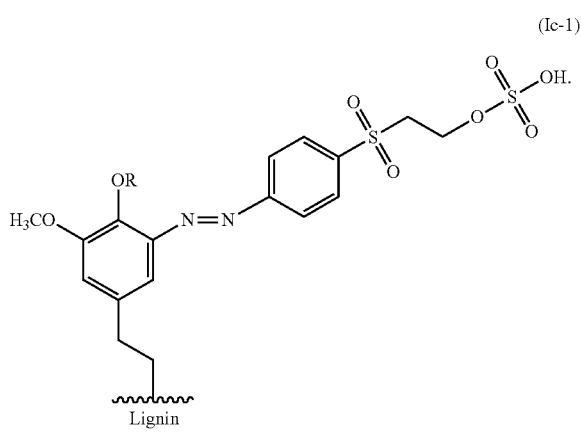

(Ic-1)

In some embodiments, the contacting is performed in an aqueous solution. The aqueous solution can have a pH of less than about 7. For example, the aqueous solution can have a pH of about 3 to about 6 or about 4 to about 5. The pH of the aqueous solution can be adjusted with a buffer such as sodium bicarbonate.

In some embodiments, the contacting is not performed in the presence of any organic solvents.

In some embodiments, the reaction of the diazonium compound with the lignin is performed for a period of less than about 5 hours, less than about 4 hours, less than about 3 hours, less than about 2 hours, or less than about 1 hour.

In some embodiments, the diazonium compound can be formed from the corresponding amine precursor prior to contacting the lignin with the diazonium compound as shown, for example, in FIG. 4. For example, the diazonium compound can be formed from the corresponding amine precursor by contacting the amine precursor with nitrous acid.

The process can further include contacting the lignin derivative with a basic aqueous solution to form an alkene lignin derivative of Formula II:

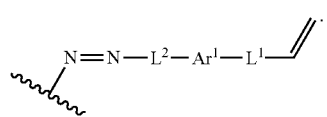

(II)

$Ar^1$ can be a 6-10 membered aryl substituted by 1, 2, 3, or 4 independently selected $R^a$ groups. $L^1$ can be selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-. $L^2$ can be selected from the group consisting of a bond, —$C_{1-6}$ alkylene-, 6-10 membered aryl, 5-10 membered heteroaryl, wherein the 6-10 membered aryl, 5-10 membered heteroaryl can be optionally substituted by 1, 2, 3, or 4 independently selected $R^b$ groups. Each Y can be independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each $R^a$ can be independently selected from the group consisting of $C_{1-6}$ alkyl, 6-10 membered aryl, 5-10 membered heteroaryl, wherein the 6-10 membered aryl, 5-10 membered heteroaryl can be optionally substituted by 1, 2, 3, or 4 independently selected $R^b$ groups. Each $R^b$ can be independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy. Each $R^c$ can be independently selected from the group consisting of H and $C_{1-3}$ alkyl. The wavy line can indicate a point of attachment to a phenyl group of the lignin.

For example, an alkene lignin derivative of Formula II can have the Formula II-1:

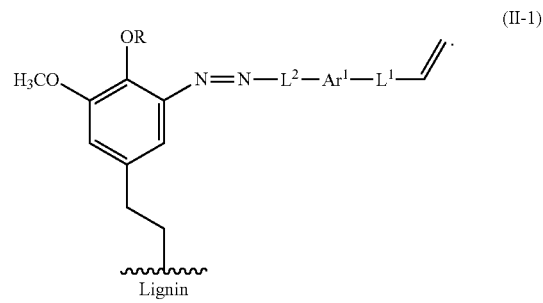

(II-1)

In some embodiments, $L^1$ is —Y— and —Y— is S(O)$_2$. In some embodiment, $L^2$ is a bond.

In some embodiments, the alkene lignin derivative of Formula II is a compound of formula IIa:

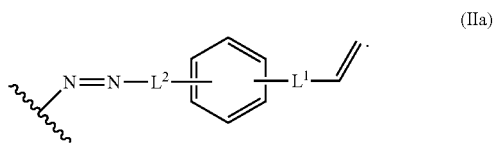

(IIa)

$L^1$ can be selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-. $L^2$ can be selected from the group consisting of a bond, —$C_{1-6}$ alkylene-, 6-10 membered aryl, 5-10 membered heteroaryl, wherein the 6-10 membered aryl, 5-10 membered heteroaryl can be optionally substituted by 1, 2, 3, or 4 independently selected $R^b$ groups. Each Y can be independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each $R^b$ can be independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy. Each $R^c$ can be independently selected from the group consisting of H and $C_{1-3}$ alkyl. The wavy line can indicate a point of attachment to a phenyl group of the lignin.

In some embodiments, $L^1$ is —Y— and —Y— is S(O)$_2$. In some embodiment, $L^2$ is a bond.

In some embodiments, the alkene lignin derivative of Formula II is a compound of formula IIb:

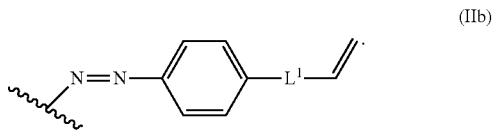

(IIb)

$L^1$ can be selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-. Each Y can be independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each R$^c$ can be independently selected from the group consisting of H and C$_{1-3}$ alkyl. The wavy line can indicate a point of attachment to a phenyl group of the lignin.

In some embodiments, the alkene lignin derivative of Formula II is a compound of formula IIc:

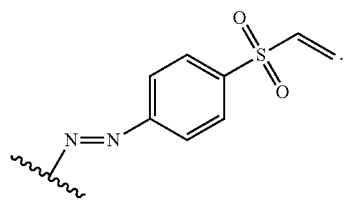

(IIc)

The wavy line can indicate a point of attachment to a phenyl group of the lignin.

For example, the alkene lignin derivative of Formula IIc can have the Formula IIc-1:

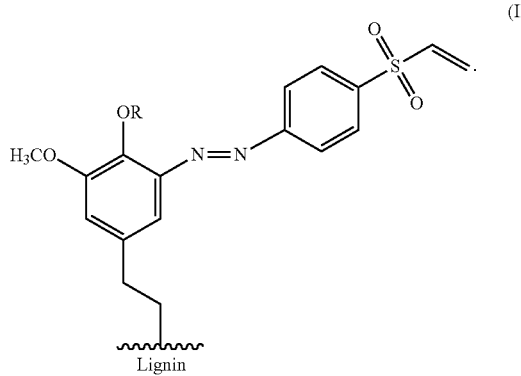

(IIc-1)

In some embodiments, the basic aqueous solution has a pH of about 8 to about 12. In some embodiments, contacting the lignin derivative with the basic aqueous solution to form the alkene lignin derivative is performed at a temperature of at least about 50° C. For example, contacting the lignin derivative with the basic aqueous solution to form the alkene lignin derivative can be performed at a temperature of about 60° C. to about 80° C.

The process can further include contacting the alkene lignin derivative with a nucleophilic compound to form a functionalized lignin. The nucleohilic compound can be any compound capable of undergoing a Michael addition with the alkene of the alkene lignin derivative (e.g., the alkene of a vinyl sulfone). In some embodiments, the nucleophilic compound can be selected from the group consisting of a polyalcohol, a sugar alcohol, a monosaccharide, a disaccharide, an oligosaccharide, a polysaccharide, a polyether, and mixtures thereof. In some embodiments, the nucleophilic compound includes at least one functional group selected from group consisting of —OH, —NH$_2$, —SH, —ONH$_2$, and —NHOH. For example, the nucleophilic compound can includes at least one functional group selected from group consisting of —OH, —NH$_2$, and —SH. The nucleophilic compound can includes at least one functional group selected from group consisting of —OH and —NH$_2$.

In some embodiments, the functionalized lignin is a compound of formula III:

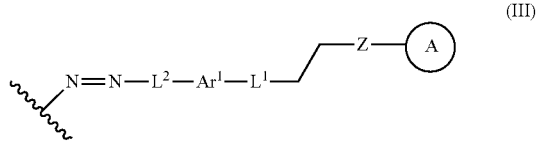

(III)

Ar$^1$ can be a 6-10 membered aryl substituted by 1, 2, 3, or 4 independently selected R$^a$ groups. L$^1$ can be selected from the group consisting of —C$_{1-6}$ alkylene-, —Y—, —Y—C$_{1-6}$ alkylene-, —Y—C$_{1-6}$ alkylene-Y—, and —C$_{1-4}$ alkylene-Y—C$_{1-4}$ alkylene-. L$^2$ can be selected from the group consisting of a bond, —C$_{1-6}$ alkylene-, 6-10 membered aryl, 5-10 membered heteroaryl, wherein the 6-10 membered aryl, 5-10 membered heteroaryl is optionally substituted by 1, 2, 3, or 4 independently selected R$^b$ groups. Each Y can be independently selected from the group consisting of O, S, S(O), S(O)$_2$, C(O), C(O)NR$^c$, NR$^c$C(O), S(O)$_2$NR$^c$, NR$^c$S (O)$_2$, and NR$^c$. Each R$^a$ can be independently selected from the group consisting of C$_{1-6}$ alkyl, 6-10 membered aryl, 5-10 membered heteroaryl, wherein the 6-10 membered aryl, 5-10 membered heteroaryl can be optionally substituted by 1, 2, 3, or 4 independently selected R$^b$ groups. Each R$^b$ can be independently selected from the group consisting of OH, NO$_2$, CN, SH, halo, C$_{1-6}$ alkyl, C$_{2-6}$ alkenyl, C$_{2-6}$ alkynyl, C$_{1-4}$ haloalkyl, and C$_{1-6}$ alkoxy. Each R$^c$ can be independently selected from the group consisting of H and C$_{1-3}$ alkyl. The wavy line can indicate a point of attachment to a phenyl group of the lignin. Z can be selected from the group consisting of —O—, —NH—, —S—, —ONH—, and —NHO—. Group A can be the nucleophilic compound.

For example, the functionalized lignin compound of Formula III can have the Formula III-1.

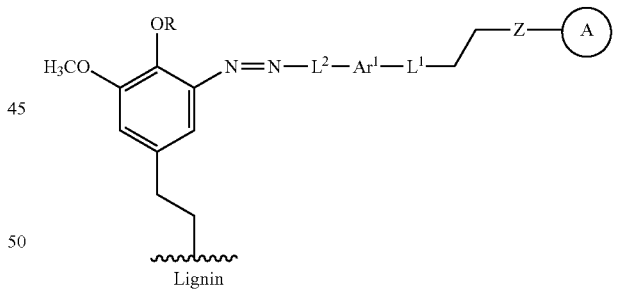

(III-1)

In some embodiments, the functionalized lignin is a compound of formula IIIa:

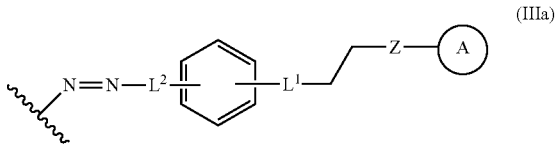

(IIIa)

L$^1$ can be selected from the group consisting of —C$_{1-6}$ alkylene-, —Y—, —Y—C$_{1-6}$ alkylene-, —Y—C$_{1-6}$ alkylene-Y—, and —C$_{1-4}$ alkylene-Y—C$_{1-4}$ alkylene-. L$^2$ can be selected from the group consisting of a bond, —$C_{1-6}$ alkylene-, 6-10 membered aryl, 5-10 membered heteroaryl, wherein the 6-10 membered aryl, 5-10 membered heteroaryl can be optionally substituted by 1, 2, 3, or 4 independently selected $R^b$ groups. Each Y can be independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each $R^b$ can be independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy. Each $R^c$ can be independently selected from the group consisting of H and $C_{1-3}$ alkyl. The wavy line can indicate a point of attachment to a phenyl group of the lignin. Z can be selected from the group consisting of —O—, —NH—, —S—, —ONH—, and —NHO—. Group A can be the nucleophilic compound.

In some embodiments, the functionalized lignin is a compound of formula IIIb:

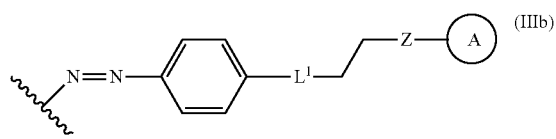

$L^1$ can be selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-. Each Y can be independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each $R^c$ can be independently selected from the group consisting of H and $C_{1-3}$ alkyl. The wavy line can indicate a point of attachment to a phenyl group of the lignin. Z can be selected from the group consisting of —O—, —NH—, —S—, —ONH—, and —NHO—. Group A can be the nucleophilic compound.

In some embodiments, the functionalized lignin is a compound of Formula IIIc:

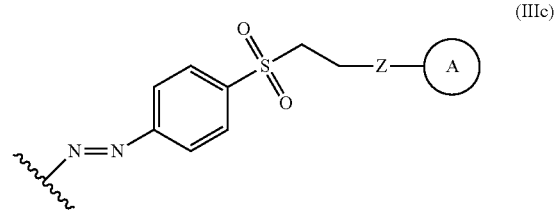

The wavy line can indicate a point of attachment to a phenyl group of the lignin. Z can be selected from the group consisting of —O—, —NH—, —S—, —ONH—, and —NHO—. Group A can be the nucleophilic compound.

For example, the functionalized lignin compound of Formula III can have the Formula IIIc-1.

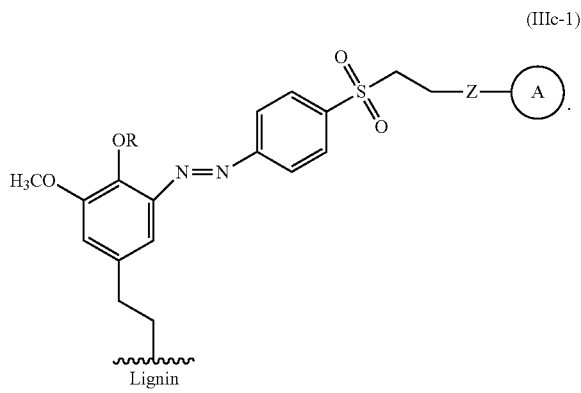

The present application provides a process for preparing a functionalized lignin. The process includes contacting a lignin with a diazonium compound of Formula I:

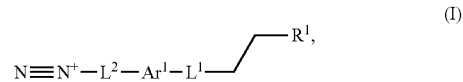

or a salt thereof, to form a lignin derivative. The process further includes contacting the lignin derivative with a basic aqueous solution to form an alkene lignin derivative of Formula II:

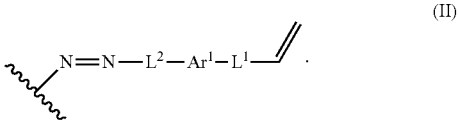

The process further includes contacting the alkene lignin derivative of Formula II with a nucleophilic compound to form a functionalized lignin via the Michael addition of the nucleophilic compound to the alkene of the lignin derivative of Formula II. $Ar^1$ is a 6-10 membered aryl substituted by 1, 2, 3, or 4 independently selected $R^a$ groups. $L^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-. $R^1$ is selected from the group consisting of —O—S(O)$_2$OH and —O—S(O)$_2$OR$^a$. $L^2$ is selected from the group consisting of a bond, —C1-6 alkylene-, 6-10 membered aryl, 5-10 membered heteroaryl, wherein the 6-10 membered aryl, 5-10 membered heteroaryl is optionally substituted by 1, 2, 3, or 4 independently selected $R^b$ groups. Each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each $R^a$ is independently selected from the group consisting of $C_{1-6}$ alkyl, 6-10 membered aryl, 5-10 membered heteroaryl, wherein the 6-10 membered aryl, 5-10 membered heteroaryl is optionally substituted by 1, 2, 3, or 4 independently selected $R^b$ groups. Each $R^b$ is independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy. Each $R^c$ is independently selected from the group consisting of H and $C_{1-3}$ alkyl. The wavy line indicates a point of attachment to a phenyl group of the lignin.

In some embodiments, the functionalized lignin is a compound of formula III:

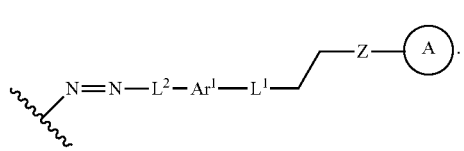

(III)

Z can be selected from the group consisting of —O—, —NH—, —S—, —ONH—, and —NHO—. Group A can be the nucleophilic compound.

The present application also provides a process for preparing a functionalized lignin. The process includes contacting a lignin with a diazonium compound of Formula Ic

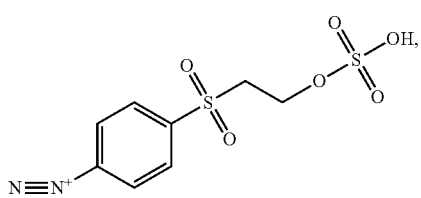

(Ic)

or a salt thereof, in an aqueous solution having a pH of about 4 to about 5 to form a lignin derivative. The process further includes contacting the lignin derivative with a basic aqueous solution at a temperature of about 60° C. to about 80° C. to form an alkene lignin derivative of Formula IIc

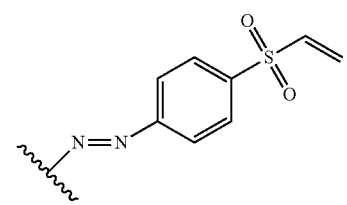

(IIc)

The wavy line indicates the point of attachment to a phenyl group of the lignin. The basic aqueous solution has a pH of about 8 to about 12. The process further includes contacting the alkene lignin derivative with a nucleophilic compound to form a functionalized lignin.

In some embodiments, the functionalized lignin is a compound of Formula IIIc:

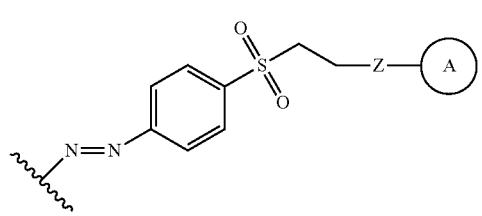

(IIIc)

The wavy line can indicate a point of attachment to a phenyl group of the lignin. Z can be selected from the group consisting of —O—, —NH—, —S—, —ONH—, and —NHO—. Group A can be the nucleophilic compound.

For example, the functionalized lignin compound of Formula III can have the Formula IIIc-1.

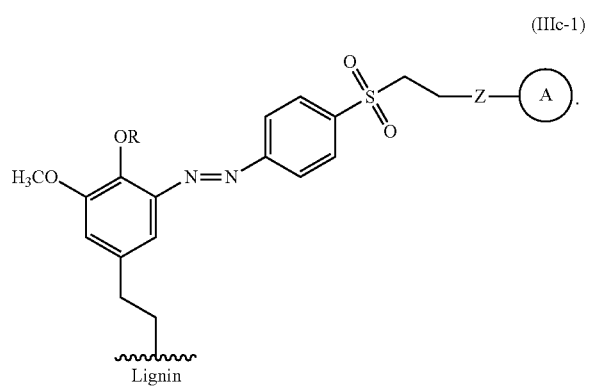

(IIIc-1)

The present application also provides a compound of Formula IV:

$$N=N-L^2-Ar^1-L^1-R^1 \quad (V)$$

$Ar^1$ is a 6-10 membered aryl substituted by 1, 2, 3, or 4 independently selected $R^a$ groups. $L^1$ is selected from the group consisting of —$C_{1-6}$ alkylene-, —Y—, —Y—$C_{1-6}$ alkylene-, —Y—$C_{1-6}$ alkylene-Y—, and —$C_{1-4}$ alkylene-Y—$C_{1-4}$ alkylene-. $R^1$ is selected from the group consisting of —O—S(O)$_2$OH and —O—S(O)$_2$OR$^a$. $L^2$ is selected from the group consisting of a bond, —C1-6 alkylene-, 6-10 membered aryl, 5-10 membered heteroaryl, wherein the 6-10 membered aryl, 5-10 membered heteroaryl is optionally substituted by 1, 2, 3, or 4 independently selected $R^b$ groups. Each Y is independently selected from the group consisting of O, S, S(O), S(O)$_2$, C(O), C(O)NR$^c$, NR$^c$C(O), S(O)$_2$NR$^c$, NR$^c$S(O)$_2$, and NR$^c$. Each $R^a$ is independently selected from the group consisting of $C_{1-6}$ alkyl, 6-10 membered aryl, 5-10 membered heteroaryl, wherein the 6-10 membered aryl, 5-10 membered heteroaryl is optionally substituted by 24 1, 2, 3, or 4 independently selected $R^b$ groups. Each $R^b$ is independently selected from the group consisting of OH, NO$_2$, CN, SH, halo, $C_{1-6}$ alkyl, $C_{2-6}$ alkenyl, $C_{2-6}$ alkynyl, $C_{1-4}$ haloalkyl, and $C_{1-6}$ alkoxy. Each $R^c$ is independently selected from the group consisting of H and $C_{1-3}$ alkyl. The wavy line indicates the point of attachment to a phenyl group of a lignin.

The present application also provides a compound of Formula V:

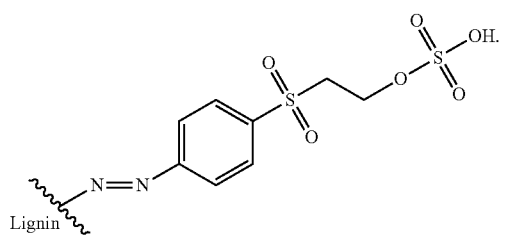

(V)

The wavy line indicates the point of attachment to a phenyl group of a lignin.

Definitions

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and naphthalene is an example of a 10-membered aryl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "halo" refers to F, Cl, Br, or I. In some embodiments, a halo is F, Cl, or Br. In other embodiments, halo is F, Cl, or I. In other embodiments, halo is F, I, or Br.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, the term "amino" refers to a group of formula —$NH_2$.

As used herein, the term "thio" refers to a group of formula —SH.

As used herein, the term "cyano" refers to a group of formula —CN.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)).

Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cyclocalkyl. In some embodiments, the cycloalkyl is a $C_{3-7}$ monocyclic cyclocalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, and the like. In some embodiments, cycloalkyl is cyclopropyl, cyclobutyl, cyclopentyl, or cyclohexyl.

As used herein, "aryl," refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein.

Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen.

In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

Part B: Bio-Based Adhesives

Bio-based adhesives are disclosed that can be made from epoxidized vegetable oils and a suitable bi-functional linker. These bio-based adhesives can be combined with one or more natural materials (e.g., renewable materials that includes cellulose, lignin, or other proteins, e.g., wood shavings, hemp) to fabricate biodegradable bio-composite materials including, for example, particle board, plywood, and cellulose-based packaging material. Importantly, both the bio-based adhesives as well as the bio-composite materials made with such bio-based adhesives are formaldehyde-free. Given the ingredients used in the bio-based adhesives described herein, they also can be used in edible compositions (e.g., as edible adhesives).

FIG. 8 is a schematic showing the reactions described herein resulting in the bio-based adhesives as well as bio-composites that include such bio-based adhesives. First, epoxidized vegetable oil (e.g., commercially available from, e.g., The Chemical Co., Jamestown, R.I.; or Arkema, France) is reacted with an excess of a suitable bi-functional linker (FIG. 8A). As shown in FIG. 8A, the suitable bi-functional linker includes vinyl sulfone precursors. As shown in FIG. 8B, the nitrogen atom of the vinyl sulfone precursors attack and open up the three membered epoxide rings in the oil by forming carbon-nitrogen covalent bonds. This leads to the incorporation of the vinyl sulfone precursor into the fatty acid side chains of the vegetable oil to form the vegetable oil-based cross-linker (FIG. 8B). It would be appreciated by a skilled artisan that follow-up treatments of this compound in the presence of a base remove the sulfonic acids. FIG. 8C shows the chemical reaction that the vegetable oil-based cross-linking agent undergoes in the presence of cellulose.

The bio-based adhesives described herein also can be used to produce other biomaterials for consumer applications such as super-absorbent materials, bio-gels, or vehicles for drug-release formulations.

Epoxidized Vegetable Oils

An example of an epoxidized vegetable oil is shown in FIG. 9. The vegetable oil shown in FIG. 9 is one embodiment of an epoxidized soybean oil. The compound is a triglyceride made up of glycerin with three fatty acid esters. The original sites of unsaturation have been converted to the reactive epoxide functional group.

In addition to the soyben oil shown in FIG. 9, a number of other vegetable oils can be used. For example, peanut oil, canola oil, crambe oil, lesquerella oil, meadowfoam oil, rapeseed oil, sunflower oil, tall oil, sesame oil, corn oil, linseed oil, or combinations thereof can be used in the bio-based adhesives described herein. It would be understood that expoxidized vegetable oils are commercially available, or, alternatively, a vegetable oil can be epoxidized using routine methods. See, for example, Saremi et al. (2012, "Epoxidation of Soybean Oil," Annals of Biol. Res., 3(9):4254-8) and Saithai et al. (2013, "Effects of different epoxidation methods of soybean oil on the characteristics of acrylated epoxidized soybean oil-co-poly(methyl methacrylate) copolymer," eXPRESS Polymer Lett., 7(11):910-24).

Vinyl Sulfone Precursors

Vinyl sulfone precursors are an inexpensive chemical commodity commonly used in the textile industry. Vinyl sulfone precursors are used herein because they have two reactive sites, one for linking to the epoxide groups of the vegetable oil and the other for linking to one or more natural materials. While there are a number of suitable vinyl sulfone precursors that are suitable for use in the bio-based adhesive described herein, the para-ester is shown, for example, in FIGS. 8 and 10. As shown in FIGS. 8 and 10, the NH$_2$ group on the vinyl sulfone precursors serves as the reactive group that is used to open the epoxide ring and form a covalent chemical bond to the vegetable oil. As described in more detail below, the vinyl sulfone precursors also have a reactive site available for reacting with one or more natural materials.

It would be appreciated that suitable bi-functional linkers for use in the methods described herein can possess other functional groups (e.g., $NH_2NH$ (a hydrazine) or OH (a phenol)) in place of the $NH_2$ group. See, for example, FIG. 10, where $R_1$ can be $NH_2$, OH, or hydrazine.

Methods of Using a Bio-Based Adhesive to Make Bio-Composite Materials

The bio-based adhesive described herein (e.g., the vegetable oil-based cross-linking agent shown in FIG. 8) can be combined with one or more natural materials. The mixture can be heated (e.g., a reaction temperature of about 35° C. to about 85° C.) under basic conditions (e.g., a pH of about 8 to about 10) to produce a bio-composite material.

As used herein, one or more natural materials typically refer to renewable natural materials. Natural materials suitable for use in the methods described herein can include, without limitation, wood chips (e.g., pinewood shavings), wood particles, or hemp. In addition, natural materials suitable for use in the methods described herein also can include, without limitation, waste material from one or more crops (e.g., cotton, corn, hay, wheat) or proteinaceous fibers such as feathers.

It would be appreciated that one or more natural materials suitable for use in the methods described herein include those materials having accessible surface hydroxyl groups and/or nucleophilic groups. While not wishing to be bound by any particular mechanism, a plurality of vinyl sulfone groups in a bio-based adhesive as described herein (see, for example, the vegetable oil-based cross-linking agent in FIG. 8) can react with a plurality of neighboring hydroxyl groups on the natural material (e.g., cellulose fibers), which forms covalent bonds and results in a rigid cross-linked structure. Under basic conditions, the vinyl sulfone precursors described herein also can react with other nucleophiles such as phenols in lignin or amino groups on protein-based substrates. The chemistry of vinyl sulfone precursors is well-documented (see, e.g., Christie, *Colour Chemistry*, In RSC Paperbacks Cambridge: Royal Society of Chemistry, 2001, e-book).

In some embodiments, high pressure can be applied to the fiber-adhesive mixture during the heating process to produce hard and higher density fiber-composite. As used herein, "high pressure" refers to a pressure of about 10 to about 2000 pounds per square inch (psi). The resulting bio-composite is non-toxic and exhibits desirable physical properties such as high strength, light weight, and biodegradability.

The methods described herein can be readily incorporated into existing production facilities with only minor modifications, and the cost of the methods and materials described herein are expected to be at or below the cost of other current formaldehyde-free adhesives or resins such as, for example, PUREBOND® or ECOSPHERE BIOPOLYMER®. The reduced costs can be attributable, at least in part, to reduced energy requirements for the present methods compared to other commercial-scale cross-linking methods. For example, the temperature for the methods disclosed herein (e.g., about 35° C. to about 85° C.) is much lower than that used in other competitive technologies (e.g., 100° C. to about 140° C., see, for example, Liu et al., 2006, J. Agric. Food Chem., 54(6):2134-7). When produced in bulk using epoxidized soybean oil, the cost for making the bio-based adhesive described herein is estimated to be about $0.80 or less per pound.

The methods described herein for making the bio-based adhesive as well as the methods described herein for using the bio-based adhesives with one or more natural materials to make bio-composite materials can be performed in water and do not require the presence of an organic solvent. Thus, the bio-composite materials produced by such methods contain no volatile organic vapors.

In accordance with the present invention, there may be employed conventional techniques within the skill of the art. Such techniques are explained fully in the literature. The invention will be further described in the following examples, which do not limit the scope of the methods and compositions of matter described in the claims.

EXAMPLES

Part A: Reactive Lignin

Example 1-Preparation of an Azo-p-Ester Lignin Polymer 4-(Ethylsulfurate sulfonyl) aniline (para-ester) (11.2 g, 0.04 mole) was added to a 250 mL Erlenmyer flask containing 50 mL of water and 15 g of ice while being stirred vigorously. Sulfuric acid ($H_2SO_4$, 9 M, 2.2 mL, 0.02 mole) was added and the mixture was then stirred for around 10 min. Sodium nitrite ($NaNO_2$, 2.76 g, 0.04 mole) was added as a solution in 20 mL water subsurface to the p-ester solution. The resulting solution mixture was stirred one additional hour at 0° C. Lignin (alkaline, 7.73 g) was then added to the solution mixture. The pH of the mixture was adjusted to 4-5 with solid sodium bicarbonate ($NaHCO_3$). The resulting solution mixture was stirred for another hour before being poured into a glass pan and dried overnight at 65° C. 21.6 g of a dark red solid product was recovered.

Part B: Bio-Based Adhesives

Example 2-Preparation of the Vegetable Oil-Based Cross-Linker Adhesive 10 g (36 mmol) of para-ester (2-((4-aminophenyl)sulfonyl)ethyl hydrogen sulfate, CAS 249489-5) was added to a 250 mL Erlenmeyer flask containing 30 mL of water and 20 g of ice. The slurry was stirred until homogeneous and 1.8 g of 50% sulfuric acid ($H_2SO_4$) was added. 2.6 g of sodium nitrite ($NaNO_2$) in 15 mL of water was added drop wise and sub-surface to the mixture. The slurry was stirred at 0° C. for one hour. 18 g of sodium sulfite ($Na_2SO_3$) in about 60 mL of water was added at 0° C. to the slurry. The pH of the mixture was adjusted to between 5 and 6 with 50% $H_2SO_4$ and the resulting solution was stirred overnight. The solution was added to a 400 mL beaker containing 9.0 g of epoxidized soybean oil (7.0% oxirane) and the mixture was stirred rapidly at 60-70° C. for 10 hr. The resulting mixture can be used as is or dried to a solid.

Example 3-Preparation of a Bio-Composite from Wood Shavings 15 g of dried vegetable oil-based cross-linker adhesive compound was added to 8 g of corn starch and 30 mL of water. The mixture was stirred for about 30 min until homogeneous. 25 g of ice was added to the mixture, followed by 15 mL of saturated aqueous sodium carbonate ($Na_2CO_3$). This mixture was added to 40 g of pine shavings, mixed well and put into a press consisting of two round metal plates and a C-clamp. The press was placed in an oven at 70° C. for two hours. The disk was cooled, and then dried at 40-50° C. overnight, yielding a solid pressed wooden disk of about 51 g. See FIG. 11.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A bioadhesive comprising an epoxidized vegetable oil and a vinyl sulfone precursor comprising an amino group and a sulfonyl group.

2. The bioadhesive of claim 1, wherein the vegetable oil is selected from the group consisting of soybean oil, peanut oil, canola oil, crambe oil, lesquerella oil, meadowfoam oil, rapeseed oil, sunflower oil, tall oil, sesame oil, corn oil, linseed oil, and combinations thereof.

3. The bioadhesive of claim 1, wherein the vinyl sulfone precursor has the structure

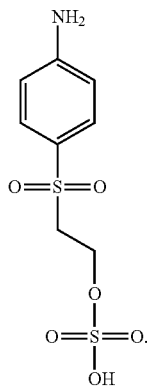 [SMILES: Nc1ccc(S(=O)(=O)CCOS(=O)(=O)O)cc1]

4. A method of making a biocomposite material, comprising combining the bioadhesive of claim 1 with a natural material to form a biocomposite material.

5. The method of claim 4, wherein the natural material is selected from the group consisting of wood shavings, wood chips, wood particles, pinewood shavings, hemp, waste cotton, and other crop wastes.

6. The method of claim 4, wherein the bio-composite material is selected from the group consisting of wood composite boards, particle board, plywood, packaging materials and edible adhesives.

7. The method of claim 4, wherein the bio-composite material is selected from the group consisting of absorbents, super-absorbents, bio-gels, and drug-release vehicles.

8. The method of claim 4, wherein the bio-composite material is formaldehyde free.

9. The method of claim 4, further comprising applying pressure.

10. The method of claim 4, wherein the combining is performed in the absence of an organic solvent.

11. The method of claim 4, wherein the vinyl sulfone precursor has the structure

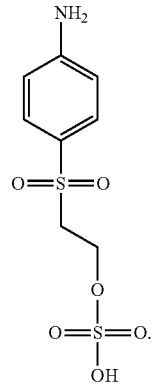 [SMILES: Nc1ccc(S(=O)(=O)CCOS(=O)(=O)O)cc1]

12. A method of making a bioadhesive, comprising combining an epoxidized vegetable oil with a vinyl sulfone precursor comprising an amino group and a sulfonyl group, thereby making a bioadhesive.

13. The method of claim 12, wherein the combining is performed under basic conditions.

14. The method of claim 13, wherein the basic conditions comprise a pH of between about 8 and about 10.

15. The method of claim 12, wherein the combining is performed under mild heat.

16. The method of claim 15, wherein the mild heat comprises a temperature of about 35° C. to about 85° C.

17. The method of claim 12, wherein the combining is performed in the absence of an organic solvent.

18. The method of claim 12, wherein the vinyl sulfone precursor has the structure

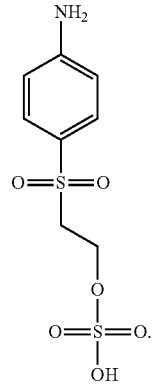 [SMILES: Nc1ccc(S(=O)(=O)CCOS(=O)(=O)O)cc1]

* * * * *